(12) United States Patent
Pagliuca et al.

(10) Patent No.: US 9,597,282 B2
(45) Date of Patent: Mar. 21, 2017

(54) COLD-WARM PLASTER

(71) Applicant: ALTERGON S.A., Lugano (CH)

(72) Inventors: Maurizio Pagliuca, Morra de Sanctis (IT); Antonio Mileo, Morra de Sanctis (IT); Danilo Truppa, Morra de Sanctis (IT); Giuseppe Bergamo, Morra de Sanctis (IT)

(73) Assignee: ALTERGON S.A., Lugano (CH)

( * ) Notice: Subject to any disclaimer, the term of this patent is extended or adjusted under 35 U.S.C. 154(b) by 0 days.

(21) Appl. No.: 14/915,746

(22) PCT Filed: Sep. 17, 2014

(86) PCT No.: PCT/EP2014/002519
§ 371 (c)(1),
(2) Date: Mar. 1, 2016

(87) PCT Pub. No.: WO2015/039748
PCT Pub. Date: Mar. 26, 2015

(65) Prior Publication Data
US 2016/0206553 A1 Jul. 21, 2016

(30) Foreign Application Priority Data

Sep. 17, 2013 (IT) .............................. MI2013A1532

(51) Int. Cl.
| | |
|---|---|
| *A01N 65/00* | (2009.01) |
| *A61K 9/00* | (2006.01) |
| *A61K 9/06* | (2006.01) |
| *A61K 9/70* | (2006.01) |
| *A61K 36/45* | (2006.01) |
| *A61F 13/02* | (2006.01) |
| *A61K 31/045* | (2006.01) |
| *A61K 31/085* | (2006.01) |
| *A61K 47/32* | (2006.01) |
| *A61K 47/38* | (2006.01) |
| *A61K 47/42* | (2006.01) |
| *A61F 13/00* | (2006.01) |

(52) U.S. Cl.
CPC ............ *A61K 9/0014* (2013.01); *A61F 13/02* (2013.01); *A61K 9/06* (2013.01); *A61K 9/7023* (2013.01); *A61K 31/045* (2013.01); *A61K 31/085* (2013.01); *A61K 36/45* (2013.01); *A61K 47/32* (2013.01); *A61K 47/38* (2013.01); *A61K 47/42* (2013.01); *A61F 2013/0071* (2013.01); *A61F 2013/00187* (2013.01); *A61F 2013/00191* (2013.01); *A61F 2013/00676* (2013.01); *A61F 2013/00748* (2013.01); *A61F 2013/00919* (2013.01)

(58) Field of Classification Search
CPC ..................................................... A61K 36/00
USPC ......................................................... 424/725
See application file for complete search history.

(56) References Cited

FOREIGN PATENT DOCUMENTS

| EP | 1568365 A1 | 8/2005 |
|---|---|---|
| WO | 2010045415 A2 | 4/2010 |

OTHER PUBLICATIONS

International Search Report from International Application No. PCT/EP2014/002519 mailed on Jan. 12, 2015.

*Primary Examiner* — Michael Meller
(74) *Attorney, Agent, or Firm* — FOX ROTHSCHILD LLP

(57) ABSTRACT

A composition for topical application characterized in that it includes, in a hydrogel base, vanillyl butyl ether and menthol. The composition described herein produces an ordered development of cold and warm sensations, obtaining effects that are particularly useful in the treatment of painful disorders of neurological and/or muscular origin. The composition has further moisturizing and soothing effects that concur to an effect that is also curative, i.e., not simply symptomatic, of rheumatic and muscular pain, trauma and bruises. The composition is compatible with each administration form, being preferably and advantageously formulated as a plaster.

1 Claim, No Drawings

COLD-WARM PLASTER

CROSS-REFERENCE TO RELATED APPLICATIONS

This application is a §371 national stage entry of International Application No. PCT/EP2014/002519 filed Sep. 17, 2014, which claims priority to Italian Application No. MI2013A001532 filed Sep. 17, 2013, both of which are hereby incorporated by reference in their entireties.

FIELD OF THE INVENTION

The present invention is in the field of the compositions for topical use, i.e., products having a localized action, useful for the treatment of painful disorders of neurological and/or muscular origin, such as rheumatic pain, lumbago, stiff neck, trauma and bruises, and further in the field of the devices suitable to the administration thereof, particularly, medicated plasters.

STATE OF THE ART

The painful disorders of neurological or muscular origin are widespread. They may have a chronic (e.g., rheumatic pain), or acute (e.g., following trauma or bruises) origin. They are more or less intense disorders, generally difficult to be treated, notably in the most acute phases. The treatment of these disorders is typically based on systemically-administered anti-inflammatory drugs, or, where applicable, locally at the affected area.

All these treatments often involve the use of significant doses of anti-inflammatory drugs, which may have undesired side-effects, especially in the case of a massive, prolonged use; an ongoing effort is thus present to reduce or even eliminate the recourse to such agents.

The above-mentioned disorders can also be treated by a local cold application, e.g., by water, ice, or through substances generating a cold sensation, such as, for example, menthol, menthane and derivatives, etc.; the thus obtained cooling reduces the painful stimulus, or at least the perception thereof. Alternatively, also the development of a warm sensation may lead to a benefit, promoting a relaxing and decontraction of the affected muscle areas.

Different devices applicable to a patient's body to generate cold or warm sensations are known. For example, packs are known, containing liquids having a high thermal capacity, which may be preventively heated or cooled, then applied onto the part of the body in need of the treatment, so as to generate the respective temperature effects. The state of the art EP 988852 shows cooling compositions based on a component selected from menthol, isopulegol, 3-methoxypropane-1,2 diol, p-menthan-3,8 diol, mixed with vanillyl butyl ether; the second component is known to cause a warm sensation; however the compositions described therein are intended only for cooling, while the heating effect is not obtained, or only occasionally in a random, non-significant statistically manner.

The publication WO-A2-2010045415 describes a topical NSAID composition, in which the addition of sensate agents such as vanillyl butyl ether improves the rate of absorption of the NSAID; the document further describes the pain relief activity for the overall NSAID composition; no specific activity on pain relief is disclosed for the sensate agents themselves; no studies are present on the timing of possible warming/cooling effects.

Since the warm/cold effects are clearly mutually opposite, there are difficulties in reconciling in a single device the generation of cold and heat. Moreover, even for devices capable to generate both sensations, it remains difficult to control their development in modes and times useful for an efficient treatment of painful disorders. Moreover, it remains a challenge to develop remedies topically effective on painful conditions, which avoid or strongly reduce the use of conventional anti-inflammatory agents.

SUMMARY

A new composition for topical application is described, characterized in that it includes, in a hydrogel base, vanillyl butyl ether and menthol. These two components, when dispersed in the hydrogel phase, at particular mutual and absolute weight ratios, allow an ordered development of cold and warm sensations, thus obtaining effects particularly useful to the treatment of painful disorders of neurological and/or muscular origin. The composition, once applied onto the skin, generates an immediate cold sensation, followed, in an ordered and statistically reproducible manner, by a warm sensation. The initial cooling effect inhibits the acute painful symptom, involving a well-being for the patient; subsequently, after the painful stimulus has been reduced/inhibited, the composition develops a pleasant warm sensation and promotes relaxation and decontraction of the affected part. Furthermore, the composition has moisturizing and soothing effects that synergize with the above-mentioned ordered cold/warm sensations, thus concurring to a curative effect, i.e. not simply symptomatic, of rheumatic and muscular pain, trauma and bruises. The composition, compatible with any administration form, is preferably and advantageously formulated as a plaster.

DETAILED DESCRIPTION OF THE INVENTION

The term "hydrogel" as used herein means a gelified phase obtained by hydration of one or more neutral or ionic homopolymers or copolymers, typically comprising hydrophilic groups (for example, hydroxy groups), having a structure of a tridimensional network, generally obtained by crosslinking reactions. Any dermocompatible, synthetic or natural hydrogel may be used as a base to disperse menthol and vanillyl butyl ether of the present invention. Among the synthetic hydrogels, mention may be made, for example, of hydrogels of: polyacrylates, such as polymers of hydroxyethyl methacrylate (HEMA), hydroxyethoxyethyl methacrylate (HEEMA), hydroxydiethoxyethyl methacryate (HDEEMA), methoxyethyl methacrylate (MEMA), methoxyethoxyethyl methacrylate (MEEMA), methoxydiethoxyetil methacrylate (MDEEMA) or sodium poliacrylate; polyethylene glycol and derivatives thereof, for example, polyethylene glycol acrylate, polyethylene glycol diacrylate, polyethylene glycol methacrylate, polyethylene glycol dimethacrylate; polyvinyl alcohol; polyvinylpyrrolidone, cross-linked or non-cross-linked; polyimide; polyacrylamide; polyurethane; cellulose gel or derivatives thereof, for example, hydroxyethyl cellulose, hydroxypropyl cellulose, hydroxypropylmethyl cellulose, cellulose acetate, carboxymethyl cellulose (Carmellose Sodium), etc. Among the natural hydrogels, hydrogels may be used, for example, of: hyaluronic acid, chitosan, gelatin, agar, collagen, dextran, etc. Preferred hydrogels are those based on gelatin, polyvinyl pyrrolidone, sodium polyacrylate, and carboxymethyl cellulose.

The dry phase of the hydrogel, i.e., the sum of all the gelling agents used, excluding water, is present in a weight ratio comprised between 35:1 and 2:1, with respect to the sum of vanillyl butyl ether and menthol (thermal-active ingredients). The hydration rate in the mixture (weight percentage of water with respect to the total composition) of the present compositions is generally comprised between 20% and 55%, preferably between 25% and 50%, more preferably about 40%.

Typically in the invention, the cooling agent menthol is present is a higher amount, compared to warming agent vanillyl butyl ether. In particular, vanillyl butyl ether and menthol are present in a relative weight ratio comprised between 1:2 and 1:25, preferably between 1:3 and 1:15. In the final hydrated composition, vanillyl butyl ether is preferably present in a weight percentage comprised between 0.01 and 1%, menthol is preferably present in a weight percentage comprised between 0.1 and 10%.

Menthol and vanillyl butyl ether are used for their respective cooling and heating properties, per se known. However, the development times of the two opposite sensations plays a key role for the usefulness of the compositions for a therapeutic purpose, allowing these two components to perform an efficient curative treatment of painful disorders of neurological/muscular orgin. In particular, it has been found that these two components, when homogeneously dispersed in certain ratios within a hydrogel phase according to the invention, obtain an ordered and reproducible development of cold and warm sensations: particularly, a first immediate cold sensation is obtained which reduces/inhibits the painful, neurologic or muscular symptom in the application zone; subsequently, about 20-30 minutes after application, a warm sensation with relaxing effect ensues; the warm sensation is perceived herein in a particularly pleasant manner, since it develops when the painful symptom has already been reduced/inhibited, by virtue of the first cooling step. Typically, in the present compositions, the pain reduction/inhibition effect continues for some time also after the cold sensation has ceased, thus obtaining a wider pain reduction/inhibition time window within which the warm sensation can best carry out its relaxing effects. Without wishing to be bound by theory, it is believed that the present hydrogel base, performing a parallel tissue moisturizing action, increases the intensity/efficiency of the cooling step, thus increasing the inhibition of the painful stimulus; the increased cooling effect avoids the development of a possible premature warm sensation, which would be less useful, being perceived still during the acute pain phase.

The composition may further include the active agent Wintergreen Oil: this is an aromatic essential oil, rich in methyl salicylate, extracted from the berries of plants of the species *Gaultheria*. This ingredient was found by the Applicant as a highly-performing soothing and flavouring component, particularly in combination with the present hydrogel. When present, the Wintergreen oil is preferably used in a ratio comprised between 5:1 and 1:5, with respect to the sum of menthol and vanillyl butyl ether.

Thanks to their enhanced therapeutic efficacy, the said menthol, vanillyl butyl ether and—when present—Wintergreen oil, are the "main" active agents of the composition, where "main" means that the composition does not include of further active principles topically active on painful disorders of neurological/muscular orgin; in particular the compostion does not contain further anti-inflammatory agents; alternatively, said further active principles may be present, although in a minoritary proportion with respect to the sum of menthol, vanillyl butyl ether and—when present—Wintergreen oil, in particular in a weight ratio lower than 1:8, or lower than 1:10; the present invention is in fact based on the key therapeutic role of the active ingredients mentioned above, which renders unnecessary the presence of additional therapeutic agents.

The present composition may further comprise non-active ingredients (excipients), selected as a function of the desired application form. Among them, mention can be made of humectants, e.g., polyalcohols, such as sorbitol or mannitol, or glycols; surfactants, e.g., polysorbates; preservatives, e.g., parabens; chelating agents such as, e.g., EDTA; pH adjusters, e.g., tartaric acid; mineral fillers, e.g., kaolin; pigments, e.g., titanium dioxide; cross-linkers e.g., aluminum glycinate or the like, etc.

Compositions, devised in particular but not exclusively for the implementation of medicated plasters, comprise, by weight:
warm/cold component (mixture of vanillyl butyl ether+menthol, in the above indicated mutual ratios): 0.10-10%
Wintergreen oil: 0-10%
gelling agents (excluding water): 2-23%
various excipients 30-60%
water: 20-55%

More preferred compositions for the use indicated above comprise, by weight:
warm/cold component (mixture of vanillyl butyl ether+menthol, in the above indicated mutual ratios): 0.20-5%
Wintergreen oil: 0-5%
gelling agents (excluding water): 2-16%
various excipients 30-60%
water: 20-55%

Even more preferred compositions include by weight, in addition to conventional excipients:
vanillyl butyl ether: 0.01-1%
menthol: 0.1-5%
Wintergreen oil: 0.1%-5%
gelling agents (excluding water): 2-16%
water: 20-55%.

Further preferred compositions include by weight, in addition to conventional excipients:
vanillyl butyl ether: 0.04-0.8%
menthol: 0.2-4%
Wintergreen oil: 0.1-5%
gelling agents (excluding water): 2-16%
water: 20-55%

Further compositions are illustrated in the experimental examples below.

The present compositions are suitable for the topical administration to patients affected by painful disorders of nervous or muscular origin, at the affected area. The cold/warm effect, as well as the moisturizing and pain-soothing effects, are perceived on the surface of the treated skin, and they can provide a benefit to the muscular masses. Several administration modes are contemplated, comprising the application in the form of a spreadable gel, or by suitable depot systems, e.g., a medicated plaster. The medicated plaster, preferred embodiment according to the invention, has the advantage of a simple, rapid, permanent in situ, precisely pre-dosed application mode, without dispersion of the product onto skin areas adjacent to those involved by the treatment; the hydrated gel also acts as a mild adhesive: it allows the adhesion of the plaster to the skin for the time necessary to develop the cold/warm effects, and, subsequently, the gentle and pain-free release of the plaster; it is thus possible to avoid additional adhesives, glues, and solvents often used for medicated plasters, which may irritate the skin, require an excessive stretching of the skin upon their removal, and/or leave residues onto the skin that are difficult to remove. The present invention has the further advantage of making available a remedy for treating painful conditions of neurologic or muscular origin which substantially avoids the use of conventional anti-inflammatory agents like e.g. NSAID, most of which are known for their long-term toxicity.

The invention is now described in non-limiting way by the following examples.

EXAMPLE 1

A composition for medicated plaster produced in accordance with the invention was made as follows:

| STARTING MATERIALS | COMPONENT PERCENTAGE |
|---|---|
| VBE | 0.5% |
| Menthol | 2.0% |
| Wintergreen oil (*Gaultheria* oil) | 2.0% |
| Gelatin | 3.0% |
| Povidone | 1.0% |
| Sorbitol | 24.5% |
| Kaolin | 2.5% |
| Propylene glycol | 4.0% |
| Carmellose Sodium (CMC) | 2.2% |
| Aluminum Glycinate | 0.1% |
| 1,3 Butylene glycol | 8.0% |
| Sodium polyacrylate | 2.2% |
| Purified water | 48.0% |
| Total | 100.0% |

The composition of example 1 was applied on a suitable support (non-woven fabric) and coated with a protective polypropylene liner.

The product was then applied onto the back of 6 volunteers who were asked to record, at regular intervals within a time period of 4 hours, the cold, neutral or warm sensations perceived on the treated skin area. The different sensations were classifiable on the following scale (F2)-(F1)-(0)-(C1)-(C2), where 0 represents the neutrality of the effect, F1/C1 a moderate cold/warm effect, respectively, and F2/C2 an intense cold/warm effect, respectively.

The results are illustrated in table 1:

TABLE 1

| Volunteers/ | Time (min)/ | | | | | | | | |
|---|---|---|---|---|---|---|---|---|---|
| | 0 | 5 | 10 | 20 | 30 | 60 | 120 | 180 | 240 |
| S-1 | 0 | F1 | F2 | F1 | C1 | C2 | C2 | C1 | C1 |
| S-2 | F2 | F2 | F1 | 0 | C1 | C2 | C2 | C1 | C1 |
| S-3 | F1 | F1 | 0 | C1 | C2 | C1 | C1 | C1 | 0 |
| S-4 | F2 | F1 | F1 | F1 | F1 | C1 | C2 | C1 | C1 |
| S-5 | 0 | F2 | F2 | F1 | F1 | C2 | C2 | C1 | C1 |
| S-6 | F2 | F2 | F2 | F1 | C1 | C2 | C2 | C1 | C1 |

The results illustrated in table 1 show, although within the usual variability intrinsic to this kind of test, a consistent cold perception in the first step after applying the plaster, followed by a consistent warm perception in the second part of the observation period.

EXAMPLE 2

A composition for a medicated plaster produced in accordance with the invention was made as follows:

| STARTING MATERIALS | COMPONENT PERCENTAGE |
|---|---|
| VBE | 0.06% |
| Menthol | 0.4% |
| Wintergreen oil (*Gaultheria* oil) | 2.0% |
| Gelatin | 3.0% |
| Povidone | 1.0% |
| Sorbitol | 25.5% |
| Kaolin | 1.5% |
| Propylene glycol | 4.0% |
| Carmellose Sodium (CMC) | 1.0% |
| Aluminum Glycinate | 0.02% |
| 1,3 Butylene glycol | 7.0% |
| Sodium polyacrylate | 10.0% |
| Purified water | 44.52% |
| Total | 100.0% |

The composition of example 2 was applied on a suitable support (non-woven fabric) and coated with a protective polypropylene liner.

The product was then applied onto the back of 6 volunteers who were asked to record, at regular intervals during a period of 4 hours, the cold, neutral or warm sensations perceived on the treated skin area.

The different sensations were classifiable on the following scale (F2)-(F1)-(0)-(C1)-(C2), where 0 represents the neutrality of effect, F1/C1 a moderate cold/warm effect, respectively, and F2/C2 an intense cold/warm effect, respectively.

The results are illustrated in table 2:

TABLE 2

| Volunteers | Time (min.)/ | | | | | | | | |
|---|---|---|---|---|---|---|---|---|---|
| | 0 | 5 | 10 | 20 | 30 | 60 | 120 | 180 | 240 |
| S-1 | F1 | F1 | F2 | C1 | C2 | C2 | C1 | C1 | 0 |
| S-2 | F2 | F2 | F1 | 0 | C1 | C2 | C1 | C1 | C1 |
| S-3 | F1 | F1 | 0 | C1 | C2 | C1 | C1 | C1 | C1 |
| S-4 | F2 | F1 | 0 | C1 | C2 | C2 | C1 | 0 | 0 |
| S-5 | 0 | F2 | F1 | C2 | C1 | C2 | C1 | C1 | C1 |
| S-6 | F1 | F2 | F1 | C1 | C2 | C1 | C1 | C1 | 0 |

The results illustrated in table 2 confirm, although within the usual variability intrinsic to this kind of test, a consistent cold perception in the first step after applying the plaster, followed by a consistent warm perception in the second part of the observation period.

The invention claimed is:

1. A topical composition consisting essentially of 0.01-1% vanillyl butyl ether and 0.1-10% menthol dispersed in a hydrogel, wherein said hydrogel has a water content of 20-55% and its dry phase is present in a weight ratio between 35:1 and 2:1 with respect to the sum of vanillyl butyl ether and menthol.

* * * * *